(12) United States Patent
Suchanek et al.

(10) Patent No.: US 10,449,520 B2
(45) Date of Patent: Oct. 22, 2019

(54) POROUS BODIES WITH ENHANCED CRUSH STRENGTH

(71) Applicant: Scientific Design Company, Inc., Little Ferry, NJ (US)

(72) Inventors: Wojciech L. Suchanek, Wyckoff, NJ (US); Michael Di Mare, Morristown, NJ (US); Jean Adam, Roselle, NJ (US); Paul E. Ellis, Jr., West New York, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 28 days.

(21) Appl. No.: 15/834,375

(22) Filed: Dec. 7, 2017

(65) Prior Publication Data
US 2018/0326403 A1 Nov. 15, 2018

Related U.S. Application Data

(60) Provisional application No. 62/506,328, filed on May 15, 2017.

(51) Int. Cl.
*B01J 21/04* (2006.01)
*B01J 21/12* (2006.01)
(Continued)

(52) U.S. Cl.
CPC ............ *B01J 23/688* (2013.01); *B01D 53/22* (2013.01); *B01D 53/86* (2013.01); *B01D 63/066* (2013.01);
(Continued)

(58) Field of Classification Search
CPC ... B01J 21/04; B01J 21/12; B01J 23/50; B01J 23/66; B01J 23/688; B01J 35/0006;
(Continued)

(56) References Cited

U.S. PATENT DOCUMENTS 3,563,914 A 2/1971 Wattimena
3,702,259 A 11/1972 Nielsen
(Continued)

FOREIGN PATENT DOCUMENTS

CN 101237926 A 8/2008
EP 0327356 A1 8/1989
(Continued)

OTHER PUBLICATIONS

Brunauer, S., et al., "Adsorption of Gases in Multimolecular Layers", J. Am. Chem. Soc., Feb. 1938, pp. 309-316.
(Continued)

*Primary Examiner* — Cam N. Nguyen
(74) *Attorney, Agent, or Firm* — Scully Scott Murphy and Presser

(57) ABSTRACT

A porous body with enhanced fluid transport properties and crush strength is provided. The porous body includes the porous body includes at least 80 percent alpha alumina and having a pore volume from 0.3 mL/g to 1.2 mL/g, a surface area from 0.3 m²/g to 3.0 m²/g, and a pore architecture that provides at least one of a tortuosity of 7 or less, a constriction of 4 or less and a permeability of 30 mdarcys or greater, wherein the porous body is a cylinder comprising at least two spaced apart holes that extend through an entire length of the cylinder. The porous body has a flat plate crush strength improved by more than 10% over a porous body cylinder having a same outer diameter and length, but having only a single hole.

28 Claims, 5 Drawing Sheets

(51) Int. Cl.
| | | |
|---|---|---|
| B01J 23/50 | (2006.01) | |
| B01J 23/66 | (2006.01) | |
| B01J 35/00 | (2006.01) | |
| B01J 35/10 | (2006.01) | |
| B01J 23/68 | (2006.01) | |
| C07D 301/10 | (2006.01) | |
| B01D 53/22 | (2006.01) | |
| B01D 53/86 | (2006.01) | |
| B01D 63/06 | (2006.01) | |
| B01D 69/10 | (2006.01) | |
| B01D 71/02 | (2006.01) | |
| B01J 23/89 | (2006.01) | |
| B01J 35/02 | (2006.01) | |
| B01J 37/00 | (2006.01) | |

(52) U.S. Cl.
CPC ........... *B01D 69/10* (2013.01); *B01D 71/025* (2013.01); *B01J 21/04* (2013.01); *B01J 21/12* (2013.01); *B01J 23/50* (2013.01); *B01J 23/66* (2013.01); *B01J 23/8986* (2013.01); *B01J 35/002* (2013.01); *B01J 35/0006* (2013.01); *B01J 35/023* (2013.01); *B01J 35/026* (2013.01); *B01J 35/108* (2013.01); *B01J 35/1009* (2013.01); *B01J 35/1014* (2013.01); *B01J 35/1038* (2013.01); *B01J 35/1042* (2013.01); *B01J 35/1047* (2013.01); *B01J 35/1076* (2013.01); *C07D 301/10* (2013.01); *B01D 71/022* (2013.01); *B01D 2255/104* (2013.01); *B01J 37/0018* (2013.01)

(58) Field of Classification Search
CPC ............... B01J 35/1009; B01J 35/1014; B01J 35/1038; B01J 35/1042; B01J 35/1047; B01J 35/1076
See application file for complete search history.

(56) References Cited

U.S. PATENT DOCUMENTS

| | | | | |
|---|---|---|---|---|
| 4,410,453 | A * | 10/1983 | Kiovsky | B01J 23/50 502/253 |
| 4,419,276 | A | 12/1983 | Bhasin et al. | |
| 4,761,394 | A | 8/1988 | Lauritzen | |
| 4,766,105 | A | 8/1988 | Lauritzen | |
| 4,874,879 | A | 10/1989 | Lauritizen | |
| 4,908,343 | A | 3/1990 | Bhasin | |
| 5,011,807 | A | 4/1991 | Hayden et al. | |
| 5,057,481 | A | 10/1991 | Bhasin | |
| 5,099,041 | A | 3/1992 | Hayden et al. | |
| 5,102,848 | A | 4/1992 | Soo et al. | |
| 5,112,795 | A | 5/1992 | Minahan et al. | |
| 5,155,242 | A | 10/1992 | Shankar et al. | |
| 5,187,140 | A | 2/1993 | Thorsteinson et al. | |
| 5,380,885 | A * | 1/1995 | Kemp | B01J 23/688 502/315 |
| 5,384,302 | A | 1/1995 | Gerdes et al. | |
| 5,407,888 | A | 4/1995 | Herzog et al. | |
| 5,597,773 | A * | 1/1997 | Evans | B01J 23/688 502/308 |
| 5,663,385 | A * | 9/1997 | Kemp | B01J 23/688 502/347 |
| 5,703,253 | A * | 12/1997 | Evans | B01J 23/688 502/308 |
| 5,801,259 | A | 9/1998 | Kowaleski | |
| 6,562,749 | B1 | 5/2003 | Lednor et al. | |
| 7,102,022 | B2 | 9/2006 | Evans et al. | |
| 7,439,375 | B2 * | 10/2008 | Lockemeyer | B01J 21/04 549/534 |
| 7,485,597 | B2 | 2/2009 | Lockemeyer et al. | |
| 7,560,577 | B2 * | 7/2009 | Hirota | B01J 23/50 502/117 |
| 7,714,152 | B2 * | 5/2010 | Pak | B01J 23/50 549/536 |
| 8,008,515 | B2 * | 8/2011 | Shima | B01J 23/66 502/243 |
| 8,017,546 | B2 * | 9/2011 | Shima | B01J 23/50 502/243 |
| 8,084,390 | B2 * | 12/2011 | Gerdes | B01J 23/50 502/347 |
| 8,357,813 | B2 * | 1/2013 | Gerdes | B01J 23/50 502/347 |
| 8,456,294 | B2 * | 6/2013 | Emigh | B60R 25/1004 340/539.1 |
| 8,546,294 | B2 * | 10/2013 | Liu | B01J 21/04 502/241 |
| 8,685,883 | B2 * | 4/2014 | Bryden | B01J 21/04 423/600 |
| 8,716,504 | B2 * | 5/2014 | Liu | B01J 21/04 502/241 |
| 8,871,677 | B2 * | 10/2014 | Richard | C07C 213/04 502/439 |
| 8,895,469 | B2 | 11/2014 | Chen et al. | |
| 8,937,031 | B2 | 1/2015 | Lockemeyer et al. | |
| 8,987,483 | B2 * | 3/2015 | Basrur | C07D 301/10 549/536 |
| 9,073,035 | B2 * | 7/2015 | Richard | C07D 301/10 |
| 9,339,798 | B2 * | 5/2016 | Richard | C07D 301/10 |
| 9,776,169 | B2 * | 10/2017 | Suchanek | B01J 23/50 |
| 10,040,055 | B2 * | 8/2018 | Verrier | B01J 23/50 |
| 10,124,318 | B2 | 11/2018 | Suchanek et al. | |
| 2005/0096219 | A1 | 5/2005 | Szymanski et al. | |
| 2008/0138569 | A1 | 6/2008 | Collier et al. | |
| 2009/0082584 | A1 | 3/2009 | Rizkalla et al. | |
| 2009/0227820 | A1 | 9/2009 | Pak et al. | |
| 2010/0056816 | A1 * | 3/2010 | Wallin | B01D 67/0041 549/534 |
| 2010/0267973 | A1 | 10/2010 | Liu et al. | |
| 2012/0022277 | A1 * | 1/2012 | Hashimoto | B01J 23/002 549/534 |
| 2012/0065055 | A1 | 3/2012 | Jiang et al. | |
| 2012/0108832 | A1 | 5/2012 | Chen et al. | |
| 2012/0323026 | A1 | 12/2012 | Lockemeyer et al. | |
| 2013/0231493 | A1 * | 9/2013 | Shishkov | C07D 301/10 549/513 |
| 2014/0100379 | A1 | 4/2014 | Richard et al. | |
| 2014/0187807 | A1 | 7/2014 | Pak | |
| 2015/0209774 | A1 * | 7/2015 | Richard | C07C 213/04 502/347 |
| 2015/0343433 | A1 | 12/2015 | Dobner et al. | |
| 2016/0354759 | A1 | 12/2016 | Suchanek et al. | |
| 2016/0354760 | A1 | 12/2016 | Suchanek | |
| 2018/0021755 | A1 * | 1/2018 | Suchanek | B01J 23/50 502/348 |

FOREIGN PATENT DOCUMENTS

| | | |
|---|---|---|
| GB | 1422451 | 1/1976 |
| WO | 9623585 A1 | 8/1996 |
| WO | 2004002954 A2 | 1/2004 |
| WO | 2010008919 A2 | 1/2010 |
| WO | 2014189741 A2 | 11/2014 |

OTHER PUBLICATIONS

Green, D. W., et al., "Perry's Engineering Handbook", 8th Edition, 2007, p. 5-58, McGraw-Hill.
Ghanbarian, B., et al., "Tortuosity in Porous Media: A Critical Review", Soil Science Society of America Journal, Sep. 20, 2013, pp. 1461-1477, 77.
"C Computing Algorithm for Volumetric Pressure Coefficients of Compressibility", AutoPore V Operator Manual, Micromeritics, Jun. 2014, 18 pages, Version: 1.01.
Lowell, S., et al., "Characterization of Porous Solids and Powders: Surface Area, Pore Size and Density", Springer 2006, pp. 200-203.
International Search Report dated Nov. 14, 2018, received in a corresponding foreign application.

(56) References Cited

OTHER PUBLICATIONS

Falamaki, C., et al., "Dual behavior of CaCO3 as a porosifier and sintering aid in the manufacture of alumina membrane/catalyst supports", Journal of the European Ceramic Society, accepted Oct. 25, 2003, pp. 3195-3201, 24.
European Office Action dated May 27, 2019, received in a related foreign application No. 16804376.8.
European Office Action dated May 28, 2019, received in a related foreign application No. 16804377.6.

* cited by examiner

POROUS BODIES WITH ENHANCED CRUSH STRENGTH

CROSS REFERENCE TO RELATED APPLICATION

The present invention claims the benefit of U.S. Provisional Patent Application No. 62/506,328 filed May 15, 2017, the entire content and disclosure of which is incorporated herein by reference.

FIELD OF THE INVENTION

The present invention relates to porous bodies with enhanced pore architecture and crush strength.

BACKGROUND

In the chemical industry and the chemical engineering industry, reliance is oftentimes made on using porous bodies, including porous ceramic bodies that are capable of performing or facilitating separations or reactions and/or providing areas for such separations and reactions to take place. Examples of separations or reactions include: filtration of gases and liquids, adsorption, reverse osmosis, dialysis, ultrafiltration, or heterogeneous catalysis. Although the desired physical and chemical properties of such porous bodies vary depending on the particular application, there are certain properties that are generally desirable in such porous bodies regardless of the final application in which they will be utilized.

For example, porous bodies may be substantially inert so that the porous bodies themselves do not participate in the separations or reactions taking place around, on or through them in a way that is undesired, unintended, or detrimental. In applications where it is desired to have the components that are being reacted or separated pass through, or diffuse into, the porous body, a low diffusion resistance (e.g., high effective diffusivity) would be advantageous.

In some applications, the porous bodies are provided within a reaction or separation space, and so they are desirably of high pore volume and/or high surface area, in order to improve the loading and dispersion of the desired reactants, and also to provide enhanced surface area on which the reactions or separations can take place. These applications also require sufficient mechanical integrity to avoid being damaged, i.e., crushed, chipped or cracked, during transport or placement. However, combination of high mechanical strength with high pore volume in a porous body is not easy to achieve because the strength decreases exponentially with increasing porosity.

In view of the above, there is a need for providing porous bodies that have a pore architecture that has enhanced fluid transport properties, particularly gas diffusion properties and high mechanical integrity. Moreover, there is a need for providing porous bodies that have such an enhanced pore architecture, yet exhibit enhanced crush strength.

SUMMARY

A porous body is provided that that is capable of performing or facilitating separations, or performing reactions and/or providing areas for such separations or reactions to take place. The porous body has enhanced pore architecture and crush strength.

In one embodiment of the present invention, the porous body includes at least 80 percent alpha alumina and having a pore volume from 0.3 mL/g to 1.2 mL/g, a surface area from 0.3 m$^2$/g to 3.0 m$^2$/g, and a pore architecture that provides at least one of a tortuosity of 7 or less, a constriction of 4 or less and a permeability of 30 mdarcys or greater, wherein the porous body is a cylinder comprising at least two spaced apart holes that extend through an entire length of the cylinder.

The porous body of the present invention can be used in a wide variety of applications such as, for example, as a filter, as a membrane or as a catalyst carrier. In one example, the porous body of the present invention is used as a carrier for a silver-based epoxidation catalyst. In such an embodiment, the silver-based epoxidation catalyst includes a porous body, as the catalyst carrier, that includes at least 80 percent alpha alumina and having a pore volume from 0.3 mL/g to 1.2 mL/g, a surface area from 0.3 m$^2$/g to 3.0 m$^2$/g, and a pore architecture that provides at least one of a tortuosity of 7 or less, a constriction of 4 or less and a permeability of 30 mdarcys or greater, wherein the porous body is a cylinder comprising at least two spaced apart holes that extend through an entire length of the cylinder. Such a porous body has a flat plate crush strength improved by more than 10% over a porous body cylinder with the same outer diameter and length, but comprising only a single hole. The catalyst further includes a catalytic amount of silver disposed on and/or in the porous body, and a promoting amount of one or more promoters disposed on and/or in the porous body.

DETAILED DESCRIPTION

The present invention will now be described in greater detail by referring to the following discussion and drawings that accompany the present invention. In the following description, numerous specific details are set forth, such as particular structures, components, materials, dimensions, processing steps and techniques, in order to provide an understanding of the various embodiments of the present invention. However, it will be appreciated by one of ordinary skill in the art that the various embodiments of the present invention may be practiced without these specific details. As used throughout the present invention, the term "about" generally indicates no more than ±10%, ±5%, ±2%, ±1% or ±0.5% from a number.

Porous bodies with enhanced pore architecture and their method of preparation are disclosed in U.S. Patent Application Publication Nos. 2016/0354760A1 and 2016/0354759A1, the entire content of each of the aforementioned publications is incorporated herein by reference. Such materials have high porosity and pore volume, which may lower the crush strength of the resultants porous body. Crush strength is very important as it determines mechanical integrity of a catalyst pellet prepared from a shaped porous body in industrial reactors. For example, catalyst pellets prepared from shaped porous bodies must survive a drop from at least several meters during reactor loading and then preserve their shape and physical integrity during reactor operation, which can be up to a few years.

Figure 1:
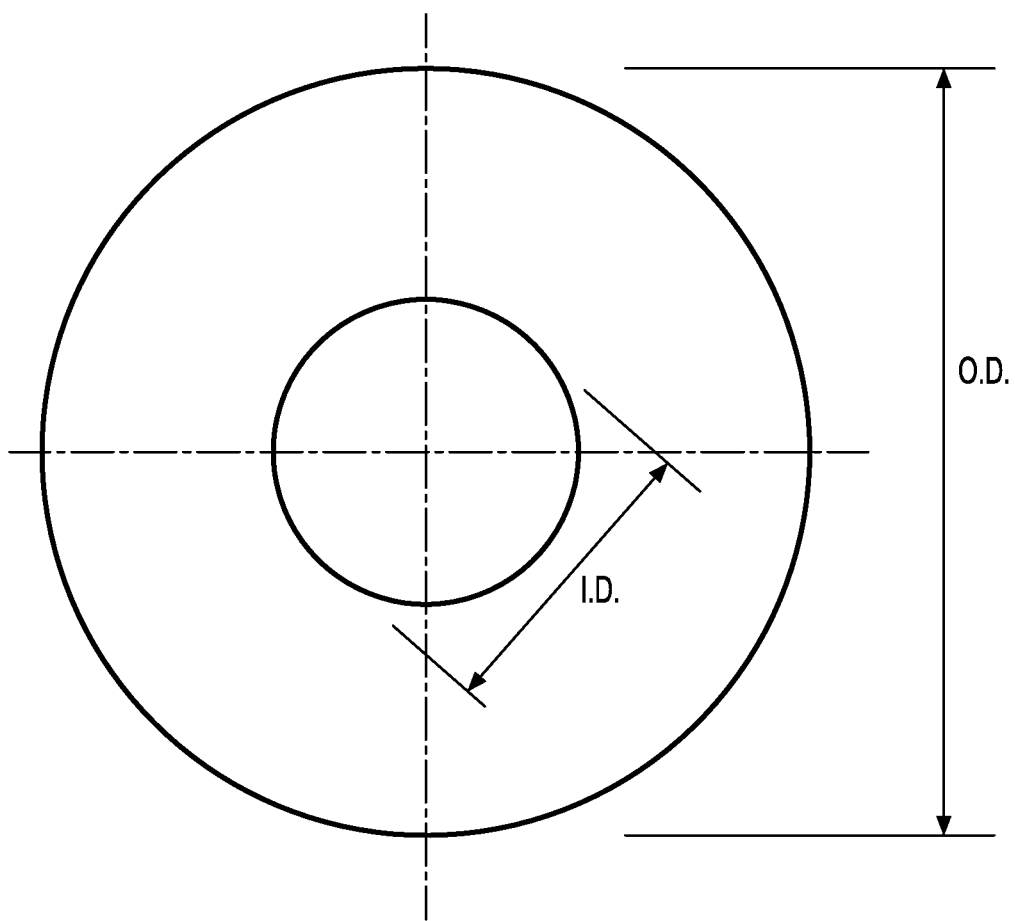
FIG. 1 is a top down view of a single-hole cylindrically shaped porous body having roughly equal length and outer diameter (so called Raschig ring) and not in accordance with the present invention.
Figure 2A:
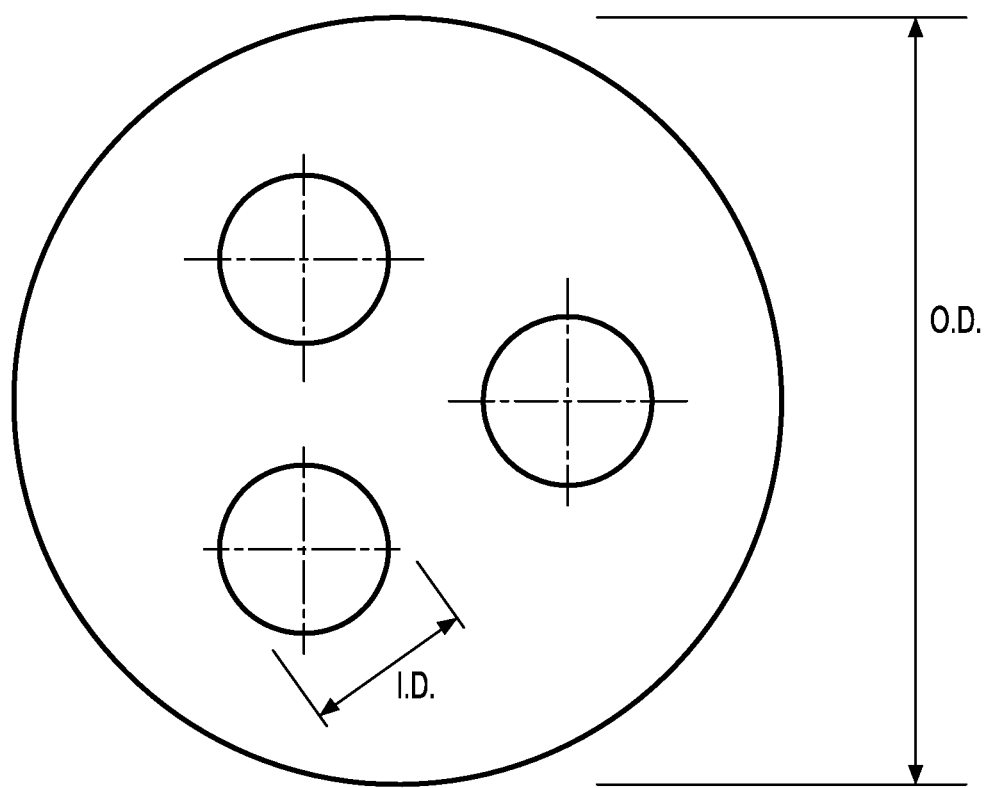
FIG. 2A is a top down view of cylindrically shaped porous body containing three holes and in accordance with the present invention.
Figure 2B:
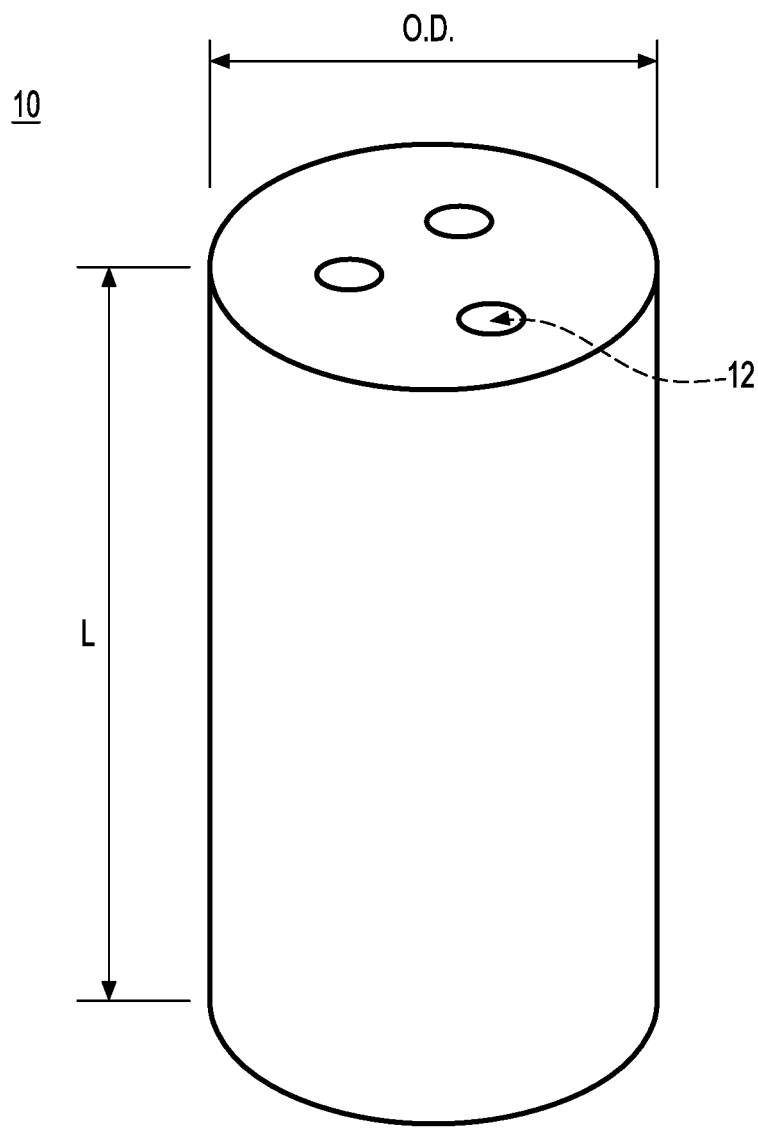
FIG. 2B is a three-dimensional representation of the cylindrically shaped porous body of FIG. 2A.
Figure 3:
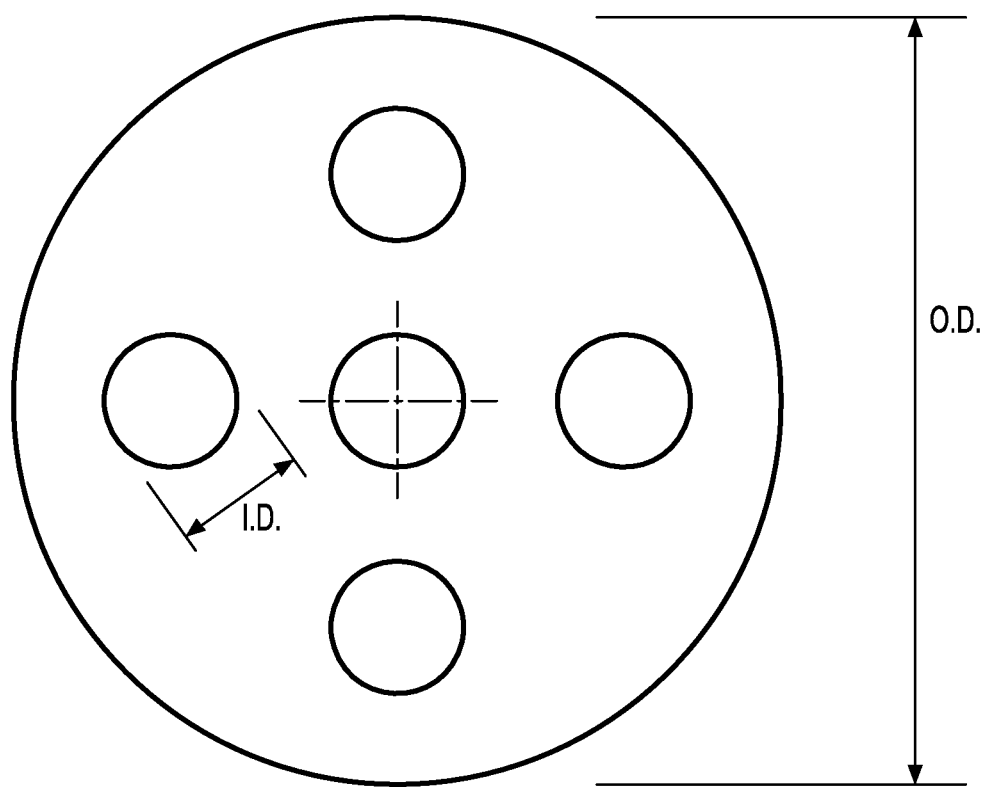
FIG. 3 is a top down view of cylindrically shaped porous body containing five holes and in accordance with the present invention.
Figure 4:
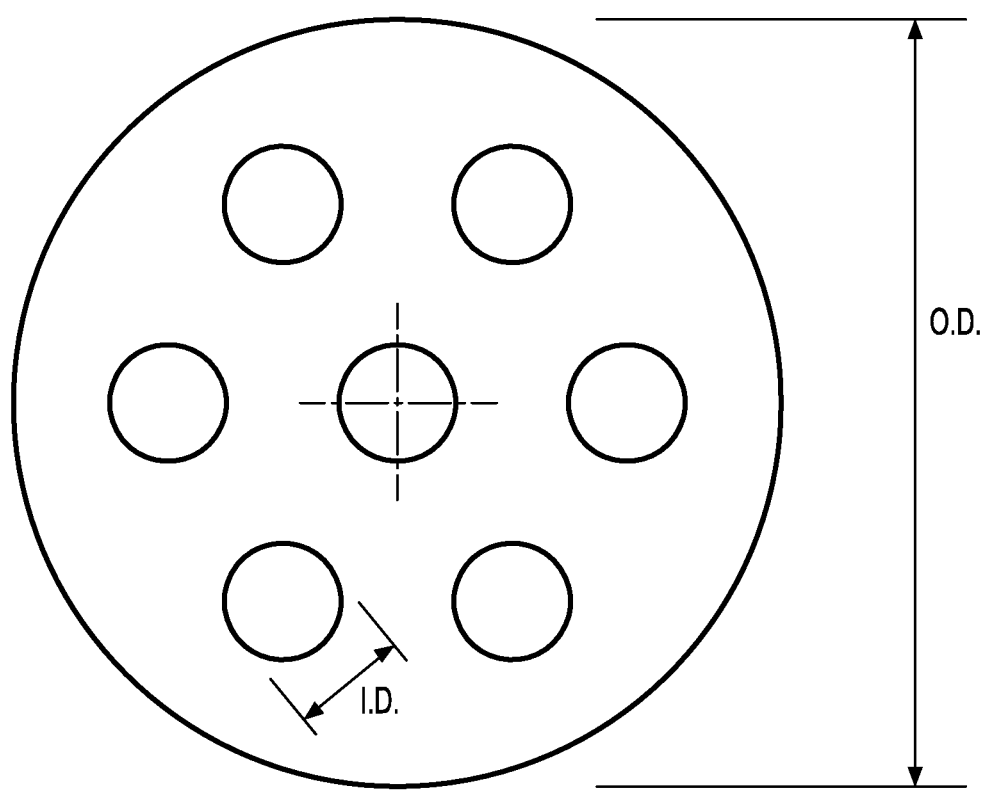
FIG. 4 is a top down view of cylindrically shaped porous body containing seven holes and in accordance with the present invention.

The present invention provides a solution to the above problem by providing a multi-hole cylindrically shaped porous body (as shown in FIGS. 2A, 2B, 3 and 4), instead of a single-hole cylindrically shaped porous body with roughly equal length and outer diameter, i.e. a typical Raschig ring, as is shown in FIG. 1. It is noted that the drawings are provided for illustration purposes only and are thus not drawn to scale. Each of the additional holes in the multi-hole cylindrically shaped porous body of the present invention is smaller in diameter than the original single hole design shown in FIG. 1. However, the total combined volume of the holes in the multi-hole cylindrically shaped porous body of the present invention is such that the pressure drop in the reactor remains the same or is comparable to the pressure drop for a single hole cylindrically shaped porous body.

According to the present invention, the average crush strength of a cylindrically shaped porous body with the same length and outer diameter is significantly improved for the multi-hole cylindrically shaped porous bodies of the present invention as compared to a single-hole cylindrically shaped porous body of the same material, same outer diameter and same length.

The porous bodies that can be employed in the present invention can be prepared by first providing a precursor mixture comprising alpha alumina powders, non-silicate binder, burn-out materials, solvents, and lubricants. An example of a non-silicate binder is boehmite (γ-AlOOH). Typically, the non-silicate binder is dispersed into deionized water or another solvent. In the present invention, the alpha alumina powder that is used in the precursor mixture is a milled alpha alumina powder that has a particle size from 0.1 microns to 6 microns. All components of the porous body precursor mixture are homogenously mixed.

In some embodiments, binders include, for example, inorganic clay-type materials, such as silica and an alkali or alkali earth metal compound. A convenient binder material which may be incorporated with the alumina particles comprises a non-silicate compound, a stabilized silica sol, and optionally alkali or alkali earth metal salt. Preferred non-silicate binders can be selected from aluminum hydroxides, oxide-hydroxides, transition aluminas, and any organic or inorganic precursors that produces alpha-alumina upon firing. In some embodiments, a silicon-containing substance is substantially or completely excluded from the method for producing the porous body. In the case of a silicon-containing substance being substantially excluded from the porous body, a trace amount of silicon derived from impurities in the raw materials used to prepare the porous body may still be present in the porous body. Such trace amounts are generally no more than 1%, 0.5%, or 0.1% by weight of the porous body.

The principle burnout material that can be used in the present invention comprises any conventional burnout material having a particle size from 1 micron to 10 microns. Some examples of burnout materials that can be used as the principle burnout material include cellulose, substituted celluloses, e.g., methylcellulose, ethylcellulose, and carboxyethylcellulose, stearates (e.g., organic stearate esters, such as methyl or ethyl stearate), waxes, granulated polyolefins (e.g., polyethylene and polypropylene), walnut shell flour, and the like, which are decomposable at the firing temperatures used in preparation of the porous body. In one example, polyethylene having a particle size from 3 microns to 8 microns can be used as the principle burnout material. In another example, paraffin or PTFE having a particle size from 1 micron to 9 microns can be used as the principal burnout material. In some embodiments, burnout materials having a decomposition of less than 550° C. (such as, for example, polyethylene and polypropylene) are preferred over burnout materials having a decomposition of 550° C. or greater (such as, for example, graphite).

In some embodiments, unmilled alpha alumina powder may be added to the precursor mixture. In other embodiments, the unmilled alpha alumina powder can be added to the precursor mixture mentioned above together with the milled alpha alumina powder. The unmilled alpha alumina powder that can be used in the present invention may have an average particle size in a range from 10 microns to 100 microns. When unmilled alpha alumina powder is employed, the weight ratio of milled alpha alumina powder to unmilled alpha alumina powder can be from about 0.25:1 to about 5:1.

An auxiliary burnout material can be optionally added to the precursor mixture. When employed, the auxiliary burnout material has a particle size that is greater than the particle size of the principle burnout material mentioned above. The auxiliary burnout material may be a same, or different, burnout material as the principle burnout material. In one example, graphite having a particle size from 3 microns to 10 microns can be used as the auxiliary burnout material. In another example, paraffin or PTFE having a particle size from 1 micron to 9 microns can be used as the auxiliary burnout material. When an auxiliary burnout material is used, the weight ratio of the principal burnout material to the auxiliary burnout material can be in a range from 1.1 to 5.4. In some embodiments, auxiliary burnout materials having a decomposition of less than 550° C. are preferred over auxiliary burnout material having a decomposition of 550° C. or greater.

In the precursor mixture mentioned above, a conventional lubricant such as, for example, Petrolatum, can be used. The amount of lubricate that can be added at this point of the present invention may comprise the total amount of, or a partial amount, of the lubricate that used in forming the porous bodies of the present invention.

In some embodiments of the present invention, additional unmilled alpha alumina powder having a larger particle size than the previously mentioned unmilled alpha alumina powder may be added to the precursor mixture. When the additional unmilled alpha alumina powder is employed, the weight ratio of milled alpha alumina powder to additional unmilled alpha alumina powder can be from about 0.2:1 to about 5:1. In some embodiments, additional lubricate can be added to the precursor mixture.

In some embodiments, the precursor mixture of the present application may also be formed utilizing the processes and materials described in U.S. Patent Application Publication No. 2016/0354759A1, the entire content of which is again incorporated herein by reference. In yet another embodiment, the precursor mixture of the present application may also be formed utilizing the processes and materials described in U.S. Ser. No. 15/834,365, now U.S. Patent Application Publication No. 2018/0326402, entitled "POROUS BODIES WITH ENHANCED PORE ARCHI- TECTURE PREPARED WITHOUT A HIGH-TEMPERATURE BURNOUT MATERIAL" filed on the same day as the present application, the entire content of which is also incorporated herein by reference.

The precursor mixture mentioned above is then formed to provide a desired shape. In the present invention, the desired shape is a cylinder comprising at least two spaced apart holes that extend through an entire length of the cylinder. By "entire length" is meant that the holes extend from a topmost surface of the cylinder to a bottommost surface of the cylinder. In one embodiment, the cylinder comprises three spaced apart holes that extend through the entire length of the cylinder. In another embodiment, the cylinder comprises five spaced apart holes that extend through the entire length of the cylinder. In a further embodiment, the cylinder comprises seven spaced apart holes that extend through the entire length of the cylinder.

FIGS. 2A, 2B, 3 and 4 illustrate cylindrically shaped porous body 10 having multiple holes 12 that extend through the entire length of the cylinder in accordance with the present invention. In the drawings, O.D. denotes outer diameter, I.D. denotes inner diameter, and L denotes the length of the cylinder. FIG. 1 shows a single-hole cylindrically shaped body which is not in accordance with the present application.

The cylinders that can be employed in the present invention have an outer diameter that can range from about 1 millimeter to about 100 millimeters. Each hole that is present in the cylinder has a same inner diameter which can range from about 0.2 millimeters to about 30 millimeters. The length of the cylinder may vary depending upon the ultimate use of the shaped porous body. In one embodiment, the cylinder may have a length from about 1 millimeter to about 100 millimeters.

The maximum number of holes that can be present in the cylinder is dependent on the outer diameter of the cylinder. In one embodiment, the cylinder has an outer diameter of from about 4 millimeters to about 10 millimeters, a length the is about equal to the outer diameter (i.e., L is from about 4 millimeters to about 10 millimeters) and the cylinder comprises three to twenty spaced holes that extend through the entire length of the cylinder. In such an embodiment, it is preferred that the cylinder contains 5 to 7 holes.

Forming of the precursor mixture into the desired shape (i.e., the multi-holed hollow cylinder described above) is typically performed by pressing, extrusion, molding, casting, etc. In one embodiment of the present invention, extruding may be performed using an extruder die that can produce cylinder shapes with multiple holes which then can be cut to pieces of substantially equal length. The extrudate after cutting is then dried using any conventional drying means. Subsequently, the dried extrudate can be transferred into a furnace in order to remove the water and burn out most of the burnout materials and other fillers that may be present. Depending on the burnout material type, heat treatment can performed at temperatures from 100° C. to 1,000° C. with heating rates varying between 10° C./hr to 100° C./hr. Subsequently, the extrudate can be sintered. In one example, sintering may be performed in flowing air at a temperature from 1200° C. to 1600° C. In some embodiments, the removal of the burnout material and the sintering may be performed in a single heat treatment process. After sintering, the resultant shaped porous body is cooled to room temperature. The heating and cooling rates can be within a range from 1° C./min up to 5° C./min. Other heating and cooling rates within a range from 0.5° C./min up to 20° C./min can also be used in the present invention for providing the porous bodies.

After sintering, shaped porous bodies as described above are provided that have an enhanced pore architecture (as defined below) and crush strength. The cylindrically shaped porous body of the present invention typically has an average flat plate crush strength that is greater than 40N. More typically, the cylindrically shaped porous body of the present invention typically has an average flat plate crush strength of from 60 N to 105 N. The flat plate crush strength of the porous bodies was measured using a standard test method for single pellet crush strength of formed catalysts and catalyst carriers, ASTM Standard ASTM D4179. As compared with a single-holed cylinder composed of the same porous body material, same outer diameter and same length, the multi-hole cylindrical porous bodies of the present invention exhibit more than 10 percent increase in average crush strength.

In order to properly characterize the cylindrically shaped porous bodies for applications in filters, membranes, or catalyst carriers, pore architecture and consequently fluid transport-related properties must also be determined.

Among very important parameters in determining the diffusive gas transport through a porous body are tortuosity and constriction. Tortuosity is determined by the ratio of the real length of flow path through a porous body to the shortest distance across that porous body (see, for example, B. Ghanbarian et al., *Soil Sci. Soc. Am. J.*, 77, 1461-1477 (2013)). Constriction is a function of the area ratio of large pores to small pores. Thus, lowering the values of tortuosity and/or constriction enhances the diffusive transport through a porous material, i.e., increases the effective diffusivity, which is very important for instance in catalytic applications.

If there is a pressure drop across the porous body, permeability becomes important. Permeability indicates ability of fluids to flow through porous bodies and can be described by the Darcy's law shown in Equation 1, where V is fluid flow velocity, k is permeability, $\mu$ is dynamic viscosity of the fluid, $\Delta P$ is pressure difference across porous body with thickness of $\Delta x$:

$$V = \frac{k}{\mu} \frac{\Delta P}{\Delta x} \qquad \text{(Eq. 1)}$$

Thus higher values of permeability will enhance the pressure-driven fluid flow across a porous body, which is important in such applications as sorption, filtration, or catalysis.

Surprisingly, the aforementioned fluid transport-determining properties of porous bodies cannot be found in the literature to characterize porous architectures, particularly as related to catalyst carriers for epoxidation of olefins. Moreover, there has been no indication in the literature of the necessary values of tortuosity, constriction or permeability which provide a pore architecture to a porous body that can achieve enhanced properties, especially in regard to catalyst performance. The present invention provides porous bodies that have a pore architecture that has enhanced fluid transport properties and high mechanical integrity.

Unless otherwise specified the following methodology of measurements were employed in the present application:

In the present invention, water absorption of the porous bodies was measured by placing a 10 g representative sample of a porous body into a flask, which was then evacuated to about 0.1 torr for 5 min. Subsequently, deionized water was aspirated into the evacuated flask to cover the porous bodies while maintaining the pressure at about 0.1 torr. The vacuum was released after about 5 minutes to restore ambient pressure, hastening complete penetration of water into the pores. Subsequently, the excess water was drained from the impregnated sample. Water absorption was calculated by dividing total water weight in the pores (i.e., wet mass–dry mass of the sample) by the weight of the dry sample at room temperature.

Cumulative intrusion curves and Log differential intrusion curves may be acquired for representative samples of the porous bodies by mercury (Hg) intrusion porosimetry, principles of which are described in Lowell et al., *Characterization of Porous Solids and Powders: Surface Area, Pore Size and Density*, Springer, 2006. The Hg intrusion pressure may range between, for example, 1.5 and 60,000 psi, which corresponds to pore sizes between 140 microns and 3.6 nm. The following Hg parameters may be used for calculations: surface tension of 480 dynes/cm, density of 13.53 g/mL, and contact angle of 140°. Pore volumes for the porous bodies may be measured from the Hg intrusion data, which are consistent with the water absorption measurements. Additional pore architecture parameters of the porous bodies, such as tortuosity, constriction, and permeability, may also be calculated from the Hg intrusion data, as discussed below.

The tortuosity, $\xi$, was calculated from Equation 2, where $D_{avg}$ is weighted average pore size, k is permeability, $\rho$ is true materials density, and $I_{tot}$ is total specific intrusion volume (see, for example, *AutoPore V Operator Manual*, Micromeritics, 2014):

$$\xi = \sqrt{\frac{D_{avg}^2}{4 \cdot 24 k (1 - \rho I_{tot})}} \quad \text{(Eq. 2)}$$

The constriction, $\sigma$, was calculated from Equation 3, where $\xi$ is tortuosity and $\tau$ is tortuosity factor, calculated from the Carnigilia equation (see, for example, *AutoPore V Operator Manual*, Micromeritics, 2014):

$$\sigma = \frac{\xi}{\tau} \quad \text{(Eq. 3)}$$

The permeability, as defined by the Darcy's law (Eq. 1, above) can be calculated by combining Darcy's and Poiseuille'd equations (see, for example, Lowell et al., *Characterization of Porous Solids and Powders*, Springer, 2006). For an arbitrary pore shape factor, f, the permeability k is expressed by Equation 4, where $\tau$ is tortuosity factor, P is materials porosity, and d is pore diameter:

$$k = \frac{P^3 d^2}{16 \, f \tau (1 - P)^2} \quad \text{(Eq. 4)}$$

Once tortuosity and pore volumes have been measured, effective diffusivity can be calculated from Equation 5, where P is materials porosity, D is diffusivity, $D_{eff}$ is effective diffusivity, and $\xi$ is tortuosity [D. W. Green, R. H. Perry, *Perry's Engineering Handbook*, 8$^{th}$ Edition, McGraw-Hill, 2007]

$$D_{eff} = \frac{PD}{\xi} \quad \text{(Eq. 5)}$$

In order to calculate absolute values of effective diffusivity, $D_{eff}$, in a porous solid, absolute values of gas diffusivity, D, must be known per Eq. 5, in addition to the material porosity and tortuosity. However, in order to compare effective diffusivity properties of different porous solids, it is possible to calculate relative numbers of effective diffusivity normalized to a standard material. With the assumption that gas diffusivity, D, is the same in all cases, it requires only knowledge of porosity and tortuosity of the porous materials (see Equation 6).

$$\frac{D_{eff,1}}{D_{eff,0}} = \frac{P_1}{\xi_1} \frac{\xi_0}{P_0} \quad \text{(Eq. 6)}$$

Total porosity is defined as the void volume divided by the total volume of the sample. It can be calculated from mercury porosimetry or water absorption, using theoretical density of the porous body.

The porous body of the present invention typically has a pore volume from 0.3 mL/g to 1.2 mL/g. More typically, the porous body of the present invention has a pore volume from 0.35 mL/g to 0.9 mL/g. In some embodiments of the present invention, the porous body of the present invention has a water absorption from 30 percent to 120 percent, with a range from 35 percent to 90 percent being more typical.

The porous body of the present invention typically has a B.E.T. surface area from 0.3 m$^2$/g to 3.0 m$^2$/g. In one embodiment, the porous body of the present invention has a surface area from 0.5 m$^2$/g to 1.2 m$^2$/g. In another embodiment body of the present invention has a surface area above 1.2 m$^2$/g up to, and including, 3.0 m$^2$/g. The B.E.T. surface area described herein can be measured by any suitable method, but is more preferably obtained by the method described in Brunauer, S., et al., *J. Am. Chem. Soc.*, 60, 309-16 (1938).

The porous body of the present invention can be monomodal, or multimodal, such as, for example, bimodal. The porous body of the present invention has a pore size distribution with at least one mode of pores in the range from 0.01 micrometers to 100 micrometers. In one embodiment of the present invention, at least 90 percent of the pore volume of the porous body is attributed to pores having a pore size of 20 microns or less. In yet another embodiment of the present invention, at least 85 percent of the pore volume of the porous body is attributed to pores having a size from 1 micron to 6 microns. In yet a further embodiment of the present invention, less than 15, preferably less than 10, percent of the pore volume of the porous body is attributed to pores having a size of less than 1 micron. In still a further embodiment of the present application at least 80 percent of the pore volume of the porous body is attributed to pores having a size from 1 micron to 10 microns. In a particular aspect of the present invention, there are essentially no pores smaller than 1 micron.

In the case of a multimodal pore size distribution, each pore size distribution can be characterized by a single mean pore size (mean pore diameter) value. Accordingly, a mean pore size value given for a pore size distribution necessarily corresponds to a range of pore sizes that results in the indicated mean pore size value. Any of the exemplary pore sizes given above can alternatively be understood to indicate a mean (i.e., average or weighted average) pore size. Each peak pore size can be considered to be within its own pore size distribution (mode), i.e., where the pore size concentration on each side of the distribution falls to approximately zero (in actuality or theoretically). The multimodal pore size distribution can be, for example, bimodal, trimodal, or of a higher modality. In one embodiment, different pore size distributions, each having a peak pore size, are non-overlapping by being separated by a concentration of pores of approximately zero (i.e., at baseline). In another embodiment, different pore size distributions, each having a peak pore size, are overlapping by not being separated by a concentration of pores of approximately zero.

In one embodiment, the porous body of the present invention may be bimodal having a first set of pores from 0.01 microns to 1 micron and a second set of pores from greater than 1 micron to 10 microns. In such an embodiment, the first set of pores may constitute less that 15 percent of the total pore volume of the porous body, while the second set of pores may constitute more than 85 percent of the total pore volume of the porous body. In yet another embodiment, the first set of pores may constitute less than 10 percent of the total pore volume of the porous body, while the second set of pores may constitute more than 90 percent of the total pore volume of the porous body.

The porous body of the present invention typically has a total porosity that is from 55 percent to 83 percent. More typically, the porous body of the present invention typically has a total porosity that is from 58 percent to 78 percent.

In some embodiments, the porous body of the present invention can have an attrition value that is less than 40%, preferably less than 25%. In some embodiments of the present invention, the porous body can have attrition less that 10%. Attrition measurements of the porous bodies were performed using a standard test method for attrition and abrasion of catalysts and catalyst carriers, ASTM Standard ASTM D4058.

In some embodiments of the present invention, the porous body of the present invention has an initial low alkali metal content. By "low alkali metal content" it is meant that the porous body contains from 2000 ppm or less, typically from 30 ppm to 300 ppm, of alkali metal therein. Porous bodies containing low alkali metal content can be obtained by adding substantially no alkali metal during the porous body manufacturing process. By "substantially no alkali metal" it is meant that only trace amounts of alkali metal are used during the porous body manufacture process as impurities from other constituents of the porous body. In another embodiment, a porous body having a low alkali metal content can be obtained by performing various washing steps to the porous body precursor materials used in forming the porous body. The washing steps can include washing in a base, water, or an acid.

In other embodiments of the present invention, the porous body has an alkali metal content that is above the value mentioned above for the porous body having substantially no alkali metal content. In such an embodiment the porous body typically contains a measurable level of sodium on the surface thereof. The concentration of sodium at the surface of the porous body will vary depending on the level of sodium within the different components of the porous body as well as the details of its calcination. In one embodiment of the present invention, the porous body has a surface sodium content of from 2 ppm to 150 ppm, relative to the total mass of the porous body. In another embodiment of the present invention, the porous body has a surface sodium content of from 5 ppm to 70 ppm, relative to the total mass of the porous body. The sodium content mentioned above represents that which is found at the surface of the porous body and that which can be leached, i.e., removed, by, for example, nitric acid (hereafter referred to as acid-leachable sodium).

The quantity of acid leachable sodium present in the porous bodies of the present invention can be extracted from the catalyst or porous body with 10% nitric acid in deionized water at 100° C. The extraction method involves extracting a 10-gram sample of the catalyst or porous body (i.e., carrier) by boiling it with a 100 ml portion of 10% w nitric acid for 30 minutes (1 atm., i.e., 101.3 kPa) and determining in the combined extracts the relevant metals by using a known method, for example atomic absorption spectroscopy (See, for example, U.S. Pat. No. 5,801,259 and U.S. Patent Application Publication No. 2014/0100379 A1).

In one embodiment of the present invention, the porous body may have a silica content, as measured as $SiO_2$, of less than 0.2, preferably less than 0.1, weight percent, and a sodium content, as measured as $Na_2O$, of less than 0.2 weight percent, preferably less than 0.1 weight percent. In some embodiments, the porous body of the present invention may have an acid leachable sodium content of 40 ppm or less. In yet further embodiments of the present invention, the porous body comprises alumina crystallites having a platelet morphology in a content of less than 20 percent by volume. In some embodiments, the alumina crystallites having a platelet morphology in a content of less than 10 percent by volume are present in the porous body of the present invention.

In addition to the above physical properties, the porous body of the present invention has a pore architecture that provides at least one of a tortuosity of 7 or less, a constriction of 4 or less and a permeability of 30 mdarcys or greater. A porous body that has the aforementioned pore architecture has enhanced fluid transport properties and high mechanical integrity. In some embodiments, and when used as a carrier for a silver-based epoxidation catalyst, a porous body having the aforementioned pore architecture can exhibit improved catalyst properties. Typically, the pore architecture of the porous body of the present invention has a tortuosity of 7 or less and/or a constriction of 4 or less.

In one embodiment of the present invention, the porous body has a pore architecture that provides a tortuosity of 7 or less. In another embodiment, the porous body of the present invention has a pore architecture that provides a tortuosity of 6 or less. In yet another embodiment, the porous body of the present invention has a pore architecture that provides a tortuosity of 5 or less. In a further embodiment, the porous body of the present invention has a pore architecture that provides a tortuosity of 3 or less. The lower limit of the tortuosity of the porous body of the present invention is 1 (theoretical limit). In some embodiments, the tortuosity can be any number bounded between 1 and 7.

In one embodiment of the present invention, the porous body has a pore architecture that provides a constriction of 4 or less. In another embodiment, the porous body of the present invention has a pore architecture that provides a constriction of 3 or less, or even 2 or less. The lower limit of the constriction of the porous body of the present invention is 1. In some embodiments, the constriction can be any number bounded between 1 and 4.

In another embodiment of the present invention, the porous body has 2-4 times improved effective gas diffusivity due to the combination of low tortuosity and high porosity.

In one embodiment, the porous body of the present invention has a pore architecture that provides a permeability of 30 mdarcys or greater. In another embodiment, the porous body of the present invention has a pore architecture that provides a permeability of 200 mdarcys or greater.

In one embodiment, the porous body contains essentially only alumina, or alumina and non-silicate binder components, in the absence of other metals or chemical compounds, except that trace quantities of other metals or compounds may be present. A trace amount is an amount low enough that the trace species does not observably affect functioning or ability of the catalyst.

In another embodiment, the porous body may be used as a catalyst carrier (i.e., catalyst support), in which case it typically contains one or more catalytically active species, typically metals, disposed on or in the porous body. The one or more catalytically active materials can catalyze a specific reaction and are well known in the art. In some embodiments, the catalytically active material includes one or more transition metals from Groups 3-14 of the Periodic Table of Elements and/or lanthanides. In such applications, one or more promoting species (i.e., species that aide in a specific reaction) can be also disposed on or in the porous body of the present invention. The one or more promoting species may be, for example, alkali metals, alkaline earth metals, transition metals, and/or an element from Groups 15-17 of the Periodic Table of Elements.

In the particular case of the porous body being used as a carrier for silver-based epoxidation catalysis, the carrier includes silver on and/or in the porous body. Thus, in the method described above, generally after the sintering step, the silver is incorporating on or into the carrier by means well known in the art, e.g., by impregnation of a silver salt followed by thermal treatment, as well known in the art, as described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. The concentration of silver salt in the solution is typically in the range from about 0.1% by weight to the maximum permitted by the solubility of the particular silver salt in the solubilizing agent employed. More typically, the concentration of silver salt is from about 0.5% by weight of silver to 45% by weight of silver, and even more typically, from about 5% by weight of silver to 35% by weight of silver by weight of the carrier. The foregoing amounts are typically also the amounts by weight found in the catalyst after thermal treatment. To be suitable as an ethylene epoxidation catalyst, the amount of silver should be a catalytically effective amount for ethylene epoxidation, which may be any of the amounts provided above.

In addition to silver, the silver-based epoxidation catalyst of the present invention may also include any one or more promoting species in a promoting amount. The one or more promoting species can be incorporated into the porous body described above either prior to, coincidentally with, or subsequent to the deposition of the silver. As used herein, a "promoting amount" of a certain component of a catalyst refers to an amount of that component that works effectively to provide an improvement in one or more of the catalytic properties of the catalyst when compared to a catalyst not containing said component.

For example, the silver-based epoxidation catalyst may include a promoting amount of a Group I alkali metal or a mixture of two or more Group 1 alkali metals. Suitable Group 1 alkali metal promoters include, for example, lithium, sodium, potassium, rubidium, cesium or combinations thereof. Cesium is often preferred, with combinations of cesium with other alkali metals also being preferred. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The silver-based epoxidation catalyst may also include a promoting amount of a Group 2 alkaline earth metal or a mixture of two or more Group 2 alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The silver-based epoxidation catalyst may also include a promoting amount of a main group element or a mixture of two or more main group elements. Suitable main group elements include any of the elements in Groups 13 (boron group) to 17 (halogen group) of the Periodic Table of the Elements. In one example, a promoting amount of one or more sulfur compounds, one or more phosphorus compounds, one or more boron compounds or combinations thereof can be used.

The silver-based epoxidation catalyst may also include a promoting amount of a transition metal or a mixture of two or more transition metals. Suitable transition metals can include, for example, the elements from Groups 3 (scandium group), 4 (titanium group), 5 (vanadium group), 6 (chromium group), 7 (manganese group), 8-10 (iron, cobalt, nickel groups), and 11 (copper group) of the Periodic Table of the Elements, as well as combinations thereof. More typically, the transition metal is an early transition metal selected from Groups 3, 4, 5, 6, or 7 of the Periodic Table of Elements, such as, for example, hafnium, yttrium, molybdenum, tungsten, rhenium, chromium, titanium, zirconium, vanadium, tantalum, niobium, or a combination thereof.

In one embodiment of the present invention, the silver-based epoxidation catalyst includes silver, cesium, and rhenium. In another embodiment of the present invention, the silver-based epoxidation catalyst includes silver, cesium, rhenium and one or more species selected from Li, K, W, Zn, Mo, Mn, and S.

The silver-based epoxidation catalyst may also include a promoting amount of a rare earth metal or a mixture of two or more rare earth metals. The rare earth metals include any of the elements having an atomic number of 57-71, yttrium (Y) and scandium (Sc). Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal. All of the aforementioned promoters, aside from the alkali metals, can be in any suitable form, including, for example, as zerovalent metals or higher valent metal ions.

The silver-based epoxidation catalyst may also include an amount of rhenium (Re), which is known as a particularly efficacious promoter for ethylene epoxidation high selectivity catalysts. The rhenium component in the catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % based on the weight of the total catalyst including the support, expressed as rhenium metal. All of these promoters, aside from the alkali metals, can be in any suitable form, including, for example, as zerovalent metals or higher valent metal ions.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated supports. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated support is typically exposed to a gas atmosphere comprising an inert gas, such as nitrogen. The inert gas may also include a reducing agent.

In another embodiment, the porous body described above can also be used as a filter in which liquid or gas molecules can diffuse through the pores of the porous body described above. In such an application, the porous body can be placed along any portion of a liquid or gas stream flow. In yet another embodiment of the present invention, the porous body described above can be used as a membrane.

In another aspect, the invention is directed to a method for the vapor phase production of ethylene oxide by conversion of ethylene to ethylene oxide in the presence of oxygen by use of the silver-based epoxidation catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

In some embodiments, the silver-based epoxidation catalyst described above exhibits a high level of selectivity in the oxidation of ethylene with molecular oxygen to ethylene oxide. For example, a selectivity value of at least about 83 mol % up to about 93 mol % may be achieved. In some embodiments, the selectivity is from about 87 mol % to about 93 mole %. The conditions for carrying out such an oxidation reaction in the presence of the silver-based epoxidation catalyst described above broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1, 2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor.

Example

In this example, various cylindrically shaped porous bodies that are composed of identical materials were prepared and the flat plate crush strength of each of the cylindrically shaped porous bodies were determined by ASTM D4179. Each of the cylindrically shaped porous bodies had the same outer diameter and length. Notably, a single hole cylindrically shaped porous body (not in accordance with the present invention), a three hole cylindrically shaped porous body (in accordance with the present invention), a five hole cylindrically shaped porous body (in accordance with the present invention), and 7 hole cylindrically shaped porous body (in accordance with the present invention) were made (using identical methods) and tested (using the same method).

The single-hole cylindrically shaped porous body had an average crush strength of 55 N (comparative example), whereas the cylindrically shaped porous body with 7 holes had an average crush strength of 77 N, which is a 40% improvement. The cylindrically shaped porous body with 5 holes had an average crush strength of 82 N, which is nearly a 50% improvement. The cylindrically shaped porous body with 3 holes had an average crush strength of 63 N, which is a 15% increase. Other material properties, such as BET surface area, pore volume, water absorption, total porosity, phase purity, chemical purity, and transport-determining pore architecture parameters, such as pore size distributions, SEM microstructure, tortuosity, constriction, permeability, etc., are the same in the Inventive Examples, and in the Comparative Example.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A porous body comprising:
at least 80 percent alpha alumina and having a pore volume from 0.3 mL/g to 1.2 mL/g, a surface area from 0.3 m²/g to 3.0 m²/g, and a pore architecture that provides at least one of a tortuosity of 7 or less, a constriction of 4 or less and a permeability of 30 mdarcys or greater, wherein said porous body is a cylinder comprising at least two spaced apart holes that extend through an entire length of the cylinder.

2. The porous body of claim 1, wherein said cylinder comprises three spaced apart holes that extend through said entire length of said cylinder.

3. The porous body of claim 1, wherein said cylinder comprises five spaced apart holes that extend through said entire length of said cylinder.

4. The porous body of claim 1, wherein said cylinder comprises seven spaced apart holes that extend through said entire length of said cylinder.

5. The porous body of claim 1, wherein said cylinder has an outer diameter of from about 4 to about 10 millimeters, said length of said cylinders is about the same as said outer diameter, and said cylinder comprises three to twenty spaced apart holes that extend through said entire length of said cylinder.

6. The porous body of claim 1, wherein each hole has an inner diameter from about 0.2 millimeters to about 30 millimeters.

7. The porous body of claim 6, wherein each cylinder has an outer diameter from about 1 millimeter to about 100 millimeters and said length of said cylinders is from about 1 millimeter to about 100 millimeters.

8. The porous body of claim 1, wherein said porous body has an average flat plate crush strength of at least 60 N.

9. The porous body of claim 1, wherein said porous body has an average flat plate crush strength improved more than 10% over a porous body cylinder with a single hole and the same outer diameter and length.

10. The porous body of claim 1, wherein said pore architecture provides said tortuosity and said constriction.

11. A silver-based epoxidation catalyst comprising:
a porous body comprises at least 80 percent alpha alumina and having a pore volume from 0.3 mL/g to 1.2 mL/g, a surface area from 0.3 m²/g to 3.0 m²/g, and a pore architecture that provides at least one of a tortuosity of 7 or less, a constriction of 4 or less and a permeability of 30 mdarcys or greater, wherein said porous body is a cylinder comprising at least two spaced apart holes that extend through an entire length of the cylinder;
a catalytic amount of silver disposed on and/or in said porous body; and
a promoting amount of one or more promoters disposed on said porous body.

12. The silver-based ethylene epoxidation catalyst of claim 11, wherein said one or more promoters comprise Group 1 alkali metal promoters, one or more transition metals, one or more Group 2 alkaline earth metals or any combination thereof.

13. The silver-based ethylene epoxidation catalyst of claim 12, wherein said one or more transition metals are selected from the group consisting of Groups 4-10 of the Periodic Table of the Elements.

14. The silver-based ethylene epoxidation catalyst of claim 13, wherein said one or more transition metals are selected from the group consisting of molybdenum, rhenium, tungsten, chromium, titanium, hafnium, zirconium, vanadium, thorium, tantalum, and niobium.

15. The silver-based ethylene epoxidation catalyst of claim 12, wherein said one or more transition metals comprise rhenium, molybdenum, tungsten, or any combination thereof.

16. The silver-based ethylene epoxidation catalyst of claim 12, wherein said Group 1 alkali metal promoters are selected from the group consisting of cesium, lithium, sodium, potassium, and rubidium.

17. The silver-based ethylene epoxidation catalyst of claim 16, wherein said Group 1 alkali metal promoters comprise lithium and cesium.

18. The silver-based ethylene epoxidation catalyst of claim 11, wherein said one or more promoters comprises a promoting combination of rhenium, cesium and lithium.

19. The silver-based ethylene epoxidation catalyst of claim 11, wherein said catalytic amount of silver is from 10 to 50% by weight.

20. The silver-based ethylene epoxidation catalyst of claim 11, wherein at least 90 percent of said pore volume is attributed to a pore size of 20 microns or less.

21. The silver-based ethylene epoxidation catalyst of claim 11, wherein at least 85 percent of said pore volume is attributed to pores having a size from 1 micron to 6 microns.

22. The silver-based ethylene epoxidation catalyst of claim 11, wherein less than 15 percent of said pore volume is attributed to pores having a size of less than 1 micron.

23. The silver-based ethylene epoxidation catalyst of claim 11, wherein at least 80 percent of said pore volume is attributed to pores having a size from 1 micron to 10 microns.

24. The silver-based ethylene epoxidation catalyst of claim 11, wherein said porous body has a silica content, as measured as $SiO_2$, of less than 0.2 weight percent, and a sodium content, as measured as $Na_2O$, of less than 0.2 weight percent.

25. The silver-based ethylene epoxidation catalyst of claim 11, wherein said porous body has a water washing acid leachable sodium content of 40 ppm or less.

26. The silver-based ethylene epoxidation catalyst of claim 11, wherein said porous body has alumina crystallites having a platelet morphology in a content of less than 20 percent by volume.

27. The silver-based ethylene epoxidation catalyst of claim 11, wherein said pore architecture provides said tortuosity and said constriction.

28. A catalyst composition comprising:
porous body comprises at least 80 percent alpha alumina and having a pore volume from 0.3 mL/g to 1.2 mL/g, a surface area from 0.3 m²/g to 3.0 m²/g, and a pore architecture that provides at least one of a tortuosity of 7 or less, a constriction of 4 or less and a permeability of 30 mdarcys or greater, wherein said porous body is a cylinder comprising at least two spaced apart holes that extend through an entire length of the cylinder; and
a catalytic amount of at least one catalytically active material disposed on and/or in said porous body.

* * * * *